United States Patent

Hogg

[11] 3,963,606
[45] June 15, 1976

[54] SEMI-AUTOMATIC ADJUSTING DELAY FOR AN ELECTRONIC PARTICLE SEPARATOR

[75] Inventor: Walter R. Hogg, Miami Lakes, Fla.

[73] Assignee: Coulter Electronics, Inc., Hialeah, Fla.

[22] Filed: June 3, 1974

[21] Appl. No.: 475,670

[52] U.S. Cl. .............................. 209/3; 209/111.5; 209/111.7 R
[51] Int. Cl.² .......................................... B07C 5/34
[58] Field of Search ............ 209/3, 4, 111.5, 111.7, 209/111.8; 324/71 CP; 356/170, 171, 39; 250/222 PC, 364

[56] References Cited
UNITED STATES PATENTS

| 3,380,584 | 4/1968 | Fulwyler | 209/3 |
|---|---|---|---|
| 3,710,933 | 1/1973 | Fulwyler et al. | 209/3 |
| 3,776,641 | 12/1973 | Northcutt et al. | 356/171 |
| 3,826,364 | 7/1974 | Bonner et al. | 209/3 |

*Primary Examiner*—Frank W. Lutter
*Assistant Examiner*—Ralph J. Hill
*Attorney, Agent, or Firm*—Silverman & Cass, Ltd.

[57] ABSTRACT

A particle separator for separating particles suspended in a fluid according to certain characteristics, including a device for adjusting an electrical delay to be equal to the time between the emergence of a particle from a jet forming aperture to the point of break-off. The device includes a variable scale graticule coupled to a potentiometer.

13 Claims, 8 Drawing Figures

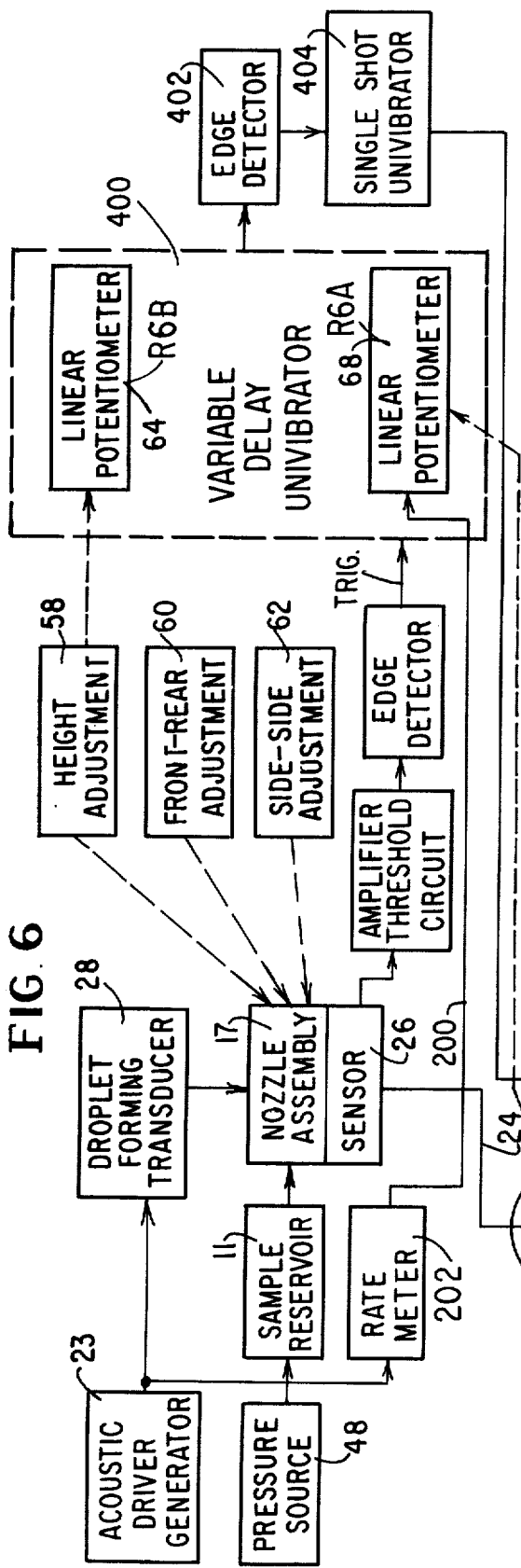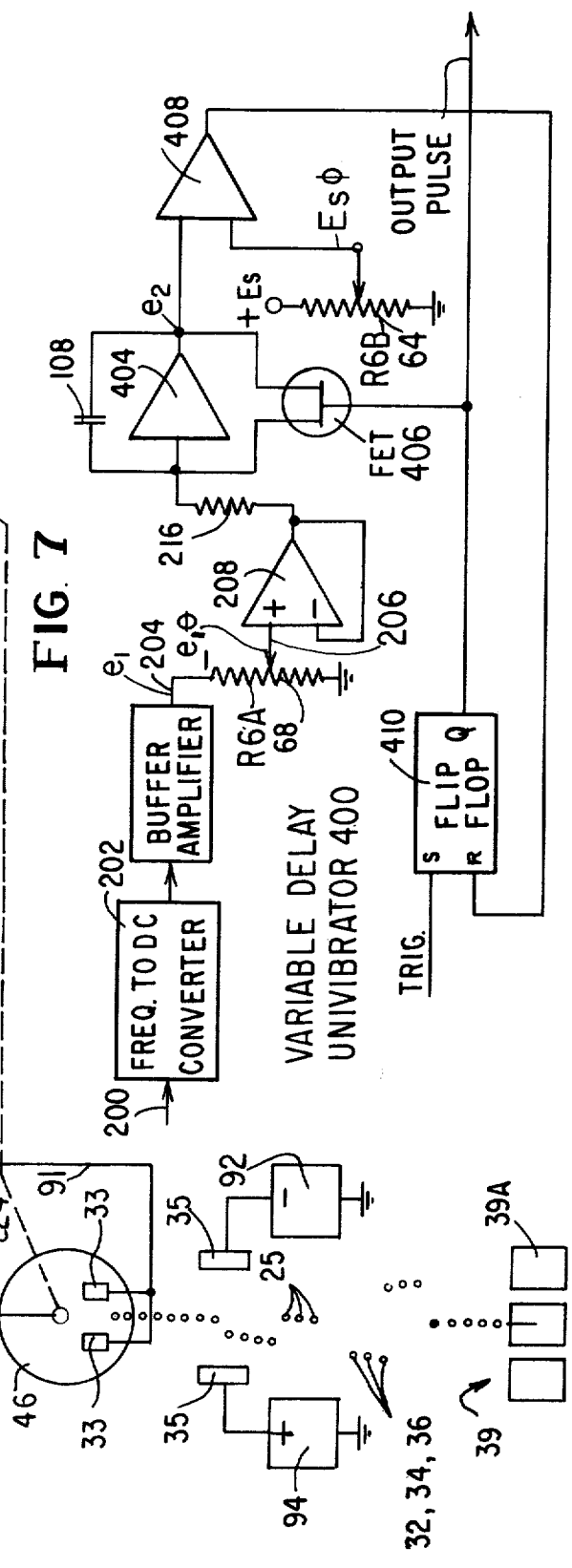

SEMI-AUTOMATIC ADJUSTING DELAY FOR AN ELECTRONIC PARTICLE SEPARATOR

CROSS-REFERENCE TO RELATED APPLICATION

The invention herein may be used in conjunction with the particle separator described in U.S. Pat. No. 3,380,584 by Mack Fulwyler.

BACKGROUND OF THE INVENTION

This invention relates to separators of particles suspended in a fluid, and in particular to a device for adjusting an electrical delay to be equal to the time between two occurrences, i.e. the passing of a particle through a sensing zone and an electric charging of the particle.

A system of particle separation was described in the above noted U.S. Pat. No. 3,380,584. To the extent that it might be necessary to understand fully the teachings of the invention herein, the above Pat. No. 3,380,584 is incorporated herein by reference.

The noted patent discloses apparatus for sorting particles in a suspension fluid in accordance with a selected characteristic which may be size, color or others. The fluid is caused to flow through an orifice to which vibration is applied. A fluid jet issuing from the orifice separates into discrete equal volume droplets. Electrostatic droplet charging means is applied to the jet downstream from the orifice where the jet separates into droplets. Furthermore, electrostatic deflecting means downstream of the charging means causes each droplet to deflect an amount related to the charge on the droplet.

DESCRIPTION OF THE PRIOR ART

In the past, trial and error procedures were used in adjusting the electric delay device. In the noted patent, the particles are sensed as they emerge from a jet-forming aperture. The jet of particle-bearing carrier liquid is broken into uniform and uniformly separated droplets by vibratory motion provided by a piezoelectric crystal. As a particle goes through the sensing zone, it causes a pulse in the associated electronics, the amplitude of which is the measure of some parameter of the particle. The particle pulse height is converted by an analog-to-digital converter and remembered by the setting of a combination of flip-flops. Simultaneously, a delay one-shot multivibrator is triggered. When the particle in the jet is further down, just before the jet breaks up into droplets, the pulse from the delay one-shot multivibrator is terminated; the trailing edge of this delay pulse is used to trigger another one-shot which gates a pulse to charging electrodes surrounding the jet having an amplitude equal to the digital-to-analog conversion of the original particle pulse height information. In later versions of the apparatus, one or more shift registers are substituted for the delay one-shot. This permits to deal with more than one particle in the jet at any given time. The pulse, at the charging electrodes, causes the droplet, which is in the process of breaking off, to have a charge such that it is several tens of volts different from the uncharged particles.

As the droplets fall, they pass through a second set of electrodes, which are at a very high DC voltage. The droplets are thereby deflected proportional to the charges on them and, hence, proportional to the pulse which had been applied to the charging electrodes. As earlier indicated the duration of the pulse of the delay one-shot must be adjusted to be equal to the time it takes a particle to get from the jet-forming aperture to the break-off point. In order to find the correct delay or pulse duration from the delay one-shot, it is necessary to try all of the possible values and observe which of them results in the droplets being deflected which contain the particles of interest.

In order for the droplets to be deflected at all, it is necessary to adjust the break-off point to occur as closely as possible to the middle of the charging electrodes.

For this purpose the Fulwyler apparatus is provided with a projection microscope illuminated by a photoflash pulse such that the jet and droplets are illuminated every 100 or other convenient number of cycles of the droplet forming frequency. This produces an image of the jet in which the droplets appear to stand still.

It is obvious that this is a long, tedious and time-consuming procedure.

SUMMARY OF THE INVENTION

A device for adjusting the electrical delay in a particle separator to be equal to the time elapsing between sensing and charging of the particles. A movable scale is used in place of the ground glass of the projection microscope of the prior art. The scale is linked to a potentiometer of a RC oscillator and thereby controls its frequency. A second potentiometer for controlling the clock oscillator frequency is coupled to a height adjustment member of the aperture.

This frequency is used to clock the delay shift registers such that the charging pulse may easily be made to occur at the appropriate time, irrespective of fluctuations of pressure, viscosity, amplitude and frequency of the droplet forming generator.

BRIEF DESCRIPTION OF THE DRAWINGS

FIG. 6 is a diagram similar to that of FIG. 3, but includes a variable delay univibrator instead of an oscillator, shift registers and a D.A. converter;

FIG. 7 is a diagram showing details of the variable delay univibrator; and

DESCRIPTION OF THE PREFERRED EMBODIMENTS

Figure 1:
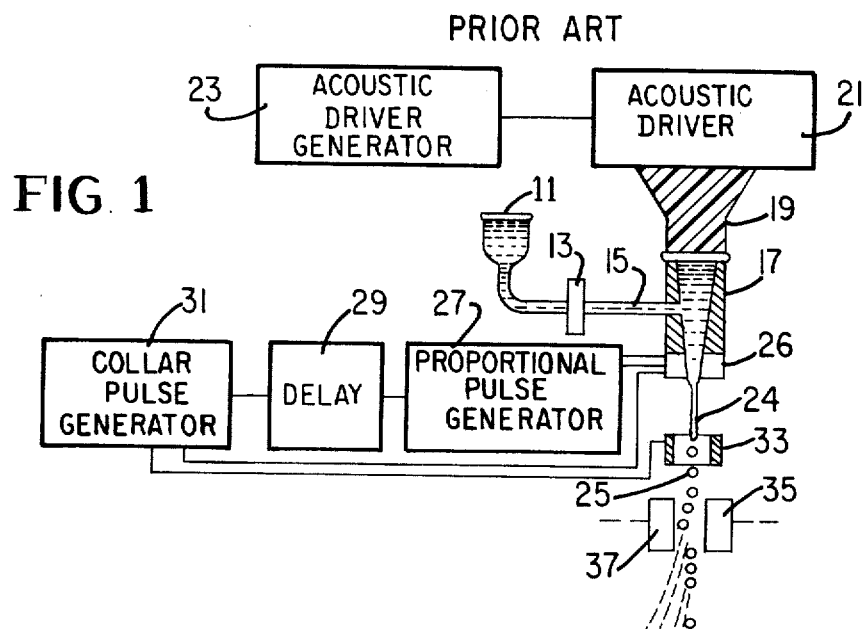
FIG. 1 shows a schematic diagram of a prior art particle separator.

In FIG. 1 a prior art particle separator as described in the above noted patent is schematically shown. Briefly, liquid containing particles in suspension is stored in a container 11 which is connected by a strainer 13 and pipe 15 to a nozzle 17. The strainer 13 is constructed to pass particles within the range of interest. An acoustic coupler 19 is driven by an electrically driven vibrator such as a piezoelectric driver 21 which in turn is energized by a frequency generator 23. Thus pulsations are applied to the fluid which in passing through the nozzle 17 forms a jet 24 which is separated into droplets 25. A sensor element 26 located at the outlet of the nozzle 17, is constructed to be responsive to a desired particle characteristic or parameter.

The electrical pulse generated in the sensor by the passage of a particle is amplified and shaped by a proportional pulse generator 27. The pulse is delayed in delay element 29 and controls the droplet charging potential produced by a collar pulse generator 31. The charging poential is inductively impressed along the jet stream between a charging collar 33 and the sensor 26. The droplets pass deflection plates 35 and 37 which are energized by a steady state potential. Each droplet is deflected an amount determined by the charge on the droplet. The droplets are segregated according to the magnitude of a selected characteristic and may be collected in a collection system 39.

As discussed earlier, the prior art method of determining the correct delay or pulse duration by trial and error is a time consuming procedure. The novel method of the instant invention represents a departure from the prior art. It proceeds from the fact that the present invention replaces or augments the ground glass of the projection microscope with a movable scale which is coupled to a linear potentiometer of a RC oscillator.

Figure 2:
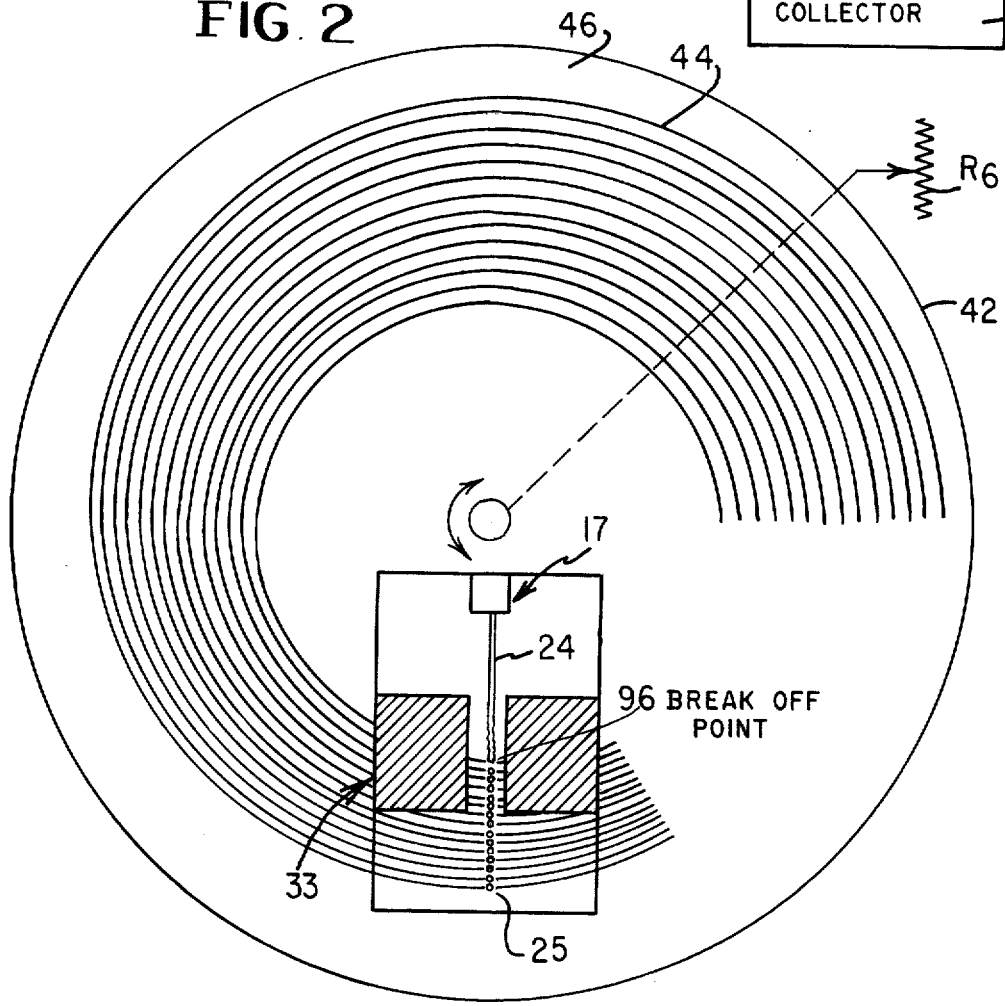
FIG. 2 illustrates an embodiment of the invention including a view of the graticule, aperture, charging electrodes, fluid jet and droplets.

FIG. 2 shows the movable graticule 42 in the form of a spiral 44 on a transparent surface to be used in conjunction with a ground glass screen 46 or it may be translucent in such a manner as to function as the ground glass screen at the same time. The nozzle 17 is behind the transparent surface 46, and the liquid jet 24 is seen leaving the nozzle and separating into droplets 25 at the breakoff point which is within the area of the charging electrodes or collar 33.

Figure 3:
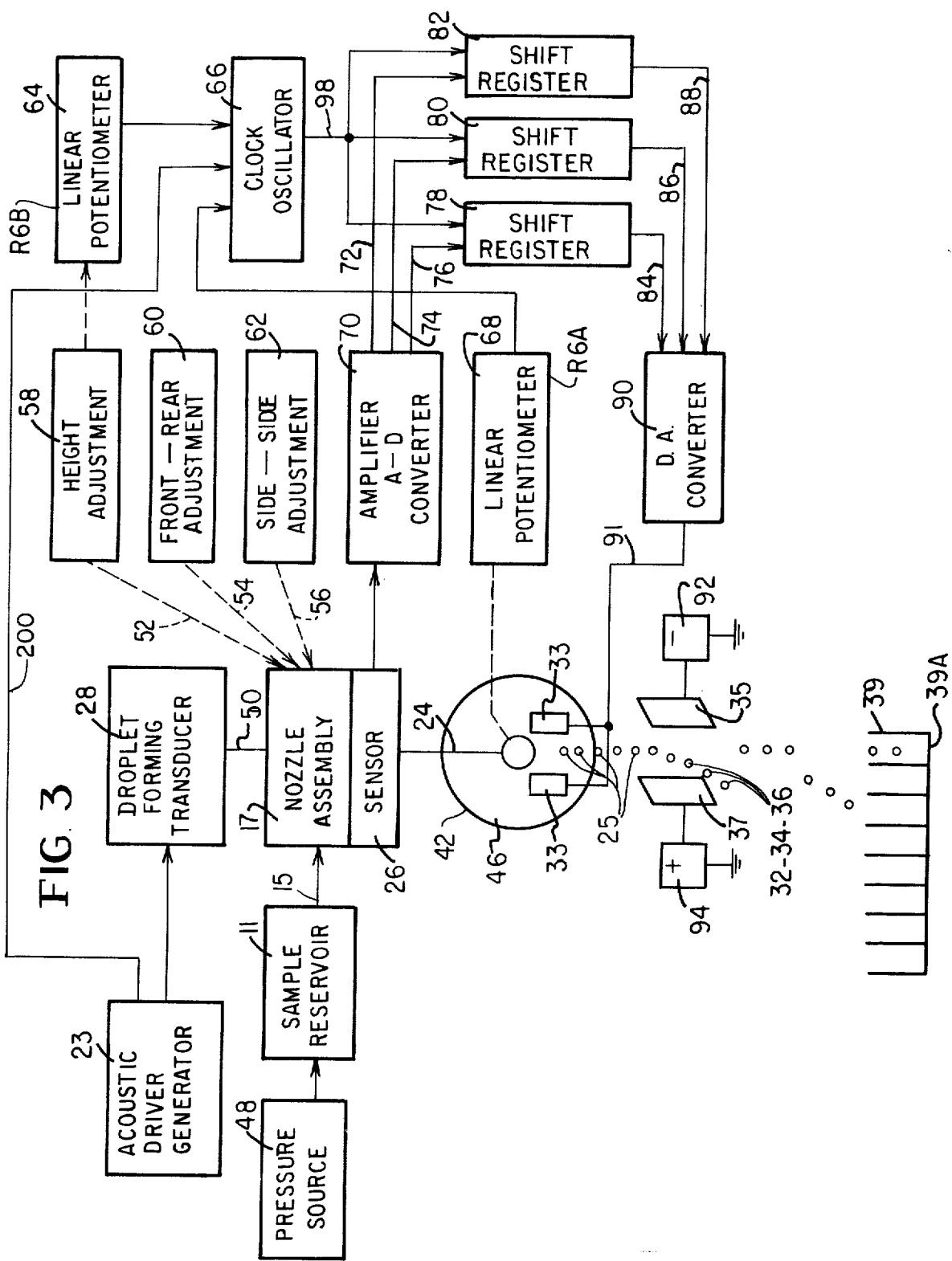
FIG. 3 is a diagram combining the prior art assembly with the delay system of the invention.

FIG. 3 is a hybrid block and schematic diagram of the entire system in which the nozzle assembly 17 and the sensor 26 are identical to those in the prior art as represented in FIG. 1. The glass screen or disc 46 of FIG. 2, the jet 24 carrying the particles and the droplets 25 are also shown, as are the charging electrodes 33 and deflecting electrodes 35 and 37. The suspension of the particles to be separated is placed in the sample reservoir 11 as in FIG. 1 and is moved by pressure from a pressure source 48 through the pipe 15 to the nozzle assembly 17 which carries the sensor 26 at the lower end thereof. Other elements shown in FIG. 1 having the same reference numerals include the acoustic driver generator 23 and the droplet forming transducer 28 connected thereto, the nozzle assembly 17 coupled via a coupling device 50 to the acoustic driver, and the collector 39 in which the droplets 25 are finally collected.

The nozzle assembly 17 is connected by lines 52, 54 and 56 to adjustment members 58, 60 and 62 for height, front-rear and side-side adjustments respectively. The height adjustment member 58 is mechanically coupled with a linear potentiometer 64 the function of which will be explained in connection with the description of FIG. 4. Although the linear potentiometer 64 is shown in the drawing as a separate block, it is actually part of a clock oscillator 66, as is also a second linear potentiometer 68 which is mechanically connected to the center of the movable graticule 42 and rotated thereby.

The sensor 26 is connected to the input side of a block 70 which includes detector circuit amplifiers and an analog to digital converter. The output side of block 70 shows three lines 72, 74 and 76 leading to first inputs of three shift registers 78, 80 and 82. The shift registers have second inputs coming in parallel from the clock oscillator 66. The output sides of the three shift registers are connected by lines 84, 86 and 88 respectively to a digital to analog converter 90, the output of which in turn is coupled to the charging electrodes 33 via line 91.

Deflecting electrodes 35 and 37 are connected to generators 92 and 94 which feed a high voltage to the electrodes 35 and 37.

In operation, the acoustic driver generator 23 supplies power supersonic frequency, for instance, 75 kilocycles which is applied via the coupling device 50 to the nozzle assembly 17, this forming the uniform, evenly spaced droplets 25. The jet 24 and the droplets 25 are shown magnified in the drawing for purposes of clarity.

The nozzle 17 which forms the jet must be placed in the exactly correct position which is accomplished by means of the three translational adjustments 58 for the height, 60 for the front to rear and 62 for the side to side motions. Once the microscope 63 is focused on the jet 24, the jet must at any later time be exactly in the right place or the image on the ground glass will be misplaced or out of focus. That is, by means of the front to rear adjustment 60, the jet is placed at the exactly optimum distance from the microscope objective lens. The assumption is made that the microscope objective is immediately in front of the jet, but mirrors or primsms may be used to make the apparatus more easily operable. By means of the side to side adjustment 62, the image is centered in the screen. The height adjustment 58 raises and lowers the nozzle 17 until the image of the break off point 96 (FIG. 2) is on the "stationary" or reference line or circle of the graticule 42. The height adjustment 58 is as earlier indicated mechanically coupled to the linear potentiometer 64 which varies the resistance R5 in the circuit of FIG. 4 to be described.

Assuming by way of example that the sensor 26 of the nozzle assembly 17 is a counter known under the trademark "Coulter Counter" and, therefore, responds to the size of particles as they emerge from the jet forming aperture, the block 70 which as indicated includes the detector circuit amplifiers and the analog to digital converter applies to lines 72, 74 and 76, a set of local ones and zeros which represent the volume of a given particle. These ones and zeros are set into the shift registers 78, 80 and 82. As the particle progresses down the jet, these ones and zeros progress down the shift registers due to the pulses from the clock oscillator 66 which are applied to all of them in parallel on path 98. Slightly before the particle has reached the break-off point 96 of the jet 24, it is desired that the ones and zeros applied on paths 72, 74 and 76 should emerge on paths 84, 86 and 88 to be immediately converted by the D to A converter 90 to an analog voltage. This is applied by way of path 91 to the charging electrodes 33.

The high voltage which deflects the charged droplets is applied by high voltage generators 92 and 94, which have opposite polarities, to the deflecting electrodes 35 and 37. Three droplets 32, 34 and 36 are shown to be deflected by the intense electric field between the electrodes 35 and 37 and will eventually fall into possibly the middle cup of the receptacle 39. Droplets containing no particles will not be charged, and will normally fall into the cup 39A of the receptacle 39.

It is apparent that the pulses at the paths 84, 86 and 88 must arrive at the same time or very slightly before the particle reaches the end of the jet 24 in order that the particle be included in the droplet which is deflected. It will also be apparent that whether or not this happens will depend upon the frequency of the clock oscillator 66, since the bits of information applied to paths 72, 74 and 76 will progress down the shift registers one step for each cycle of the clock oscillator 66.

It will be appreciated, from the preceding discussion that the problem is how to assure that the clock oscillator which causes the information to be shifted through the shift registers runs at the appropriate frequency. If the frequency is too high, the charging pulse will be applied to the charging electrodes too soon. If the frequency is too low, the particle of interest will progress to the end of the jet, be broken off into a droplet and be well downstream before the charging pulse is applied. On the other hand, all of the information needed to cause this frequency to be correct is contained in the distance between the particle sensing zone and the droplet breakoff point and the distance between the droplets. This is logically derived from the following observations.

We may assume that the particles travel with the same velocity as the electrolyte in which they are suspended. If they would have a different velocity that would lead to a form of settling; however, since the time elapsed from the sensing of the particle to the time it breaks off in one of the droplets is on the order of tens, or at most, hundreds of microseconds, the particles remain in contact with same molecules of the electrolyte for all practical purposes.

Further, it can be observed that the electrolyte or liquid carrier has the same velocity before and after breaking into droplets. This is obvious because the amount of electrolyte arriving at any height has to be exactly equal to the amount leaving that height; otherwise, electrolyte would either have to be accumulating in mid air at that height or electrolyte would have to be emanating out of mid air to continue its downward trip. Neither is there anything to absorb its kinetic energy at that height.

Also, the distance between the adjacent droplets is the distance the same droplet will travel in one cycle of the droplet forming frequency. This can be shown since it is possible to stroboscopically freeze the motion of these droplets.

If the stroboscopic lamp fires once for each cycle of the droplet forming frequency, the droplets have exactly enough time to go from one position to the next between flashes. Assuming that one looks at the enlarged image of the train of droplets on the spiral graticlue, if the droplet forming frequency is correct, a given droplet will first line up with the first spiral line on the graticule on the first flash of the light, the second line on the graticule with the second flash of the light, and so forth. Since all of the droplets are doing the same thing, it is sufficient to look at all of the droplets in one flash rather than observe the process of a given droplet with respect to the graticule.

Symbols may be assigned to the various measurements as are listed below:

x = distance between intersections of spirals and vertical lines = distance between droplets M = magnification of microscope
D = distance of breakoff point from nozzle
f = frequency of droplet formation
P = period of droplet formation = $1/f$
S = number of bits in shift register(s)
$f_c$ = clock frequency to shift register(s)
v = velocity of electrolyte or droplets
T = time elapsed as particle goes from nozzle to breakoff point We can now write the velocity of a droplet and hence the velocity of a particle. This velocity is the distance between the images of the adjacent droplets divided by the magnification of the projection microscope which very small distance is divided by the period of the droplet forming frequency, i.e., $$V = \frac{\frac{x}{M}}{P} = \frac{x}{MP} = \frac{xf}{M} \qquad 1$$

But since we know that this velocity is also equal to the velocity before the electrolyte breaks into droplets, we also know that the velocity equals the distance of the breakoff point from nozzle divided by the time elapsed as a particle goes from the nozzle divided to the breakoff point, i.e., $$V = D/T \qquad 2$$

Hence, we have two ways of expressing the same velocity, and noting that the period of the droplet formation oscillator is the reciprocal of its period, we obtain the equation 3 — $D/T = xf/M$ which can then be rearranged thus $$DM = T \times f. \qquad 3$$

In order that the droplet containing a particle of interest is charged for deflection, the number of bits in the shift registers times the period of the clock oscillator, which is the reciprocal of its frequency, must equal the time it takes for a particle to get from the nozzle to the breakoff point, that is, $S \div f_c = T$ which may be written as $$S = T \cdot f_c. \qquad 4$$

For instance, if the clock oscillator is running at a hundred kilohertz, the period is 10 microseconds. If the shift registers have each 100 stages, the total delay time is 1,000 microseconds or 1 millisecond, which is the time it takes a particle to get from the sensing zone to the breakoff point. If we substitute this value of T ($=S/f_c$) into equation 3, we find that the clock oscillator frequency, which is used to step the shift registers, is a constant determined by the number of bits S in the shift registers, the droplet forming frequency f and the magnification M of the microscope, multiplied by a variable frequency $x/D$ which is proportional to the distance $x$ between adjacent droplets and inversely proportional to the distance D from the nozzle to the breakoff point, that is, $$f_c = \frac{Sxf}{DM} = \frac{Sf}{M} \cdot \frac{x}{D} \qquad 5$$

The value of $x$ is entered into the oscillator by turning the graticule until the spiral lines line up one for one with the droplets, thus, setting the potentiometer $R_6$, and the value of D is entered into the oscillator circuit by means of the mechanical coupling between the potentiometer 64 and the height adjustment 58 of the breakoff point, see FIG. 3.

The preceeding discussion is predicated upon the assumption that the droplet forming frequency is a constant as if it were crystal controlled. If this is the case, and to illustrate the action, one assumes for example a doubling of flow rate produced by a rise of pressure, the doubled velocity would normally result in half the required delay time. If the pulsating means is able to break off a droplet for each cycle of the pulsating frequency, each droplet would have to be twice as big in volume because twice as much water would flow into it in the 10 microseconds. But the unidirectional component of the velocity of any electrolyte molecule or particle is still the same before and after it is included in a separated droplet.

So, the situation is that the droplets have twice the volume and twice the velocity, which would, other things being equal, produce twice the flow downstream from a breakoff point than it is upstream. However, the fact that the distance between the droplets is now doubled because of the doubled velocity brings the total flow of water above and below the breakoff point back into equilibrium. Since the droplets are now twice as far apart as before, the operator must turn the graticule until the spiral lines are aligned with the doubly distant droplets and, in the process, doubles the clock frequency, halving the delay time as desired.

Figure 5:
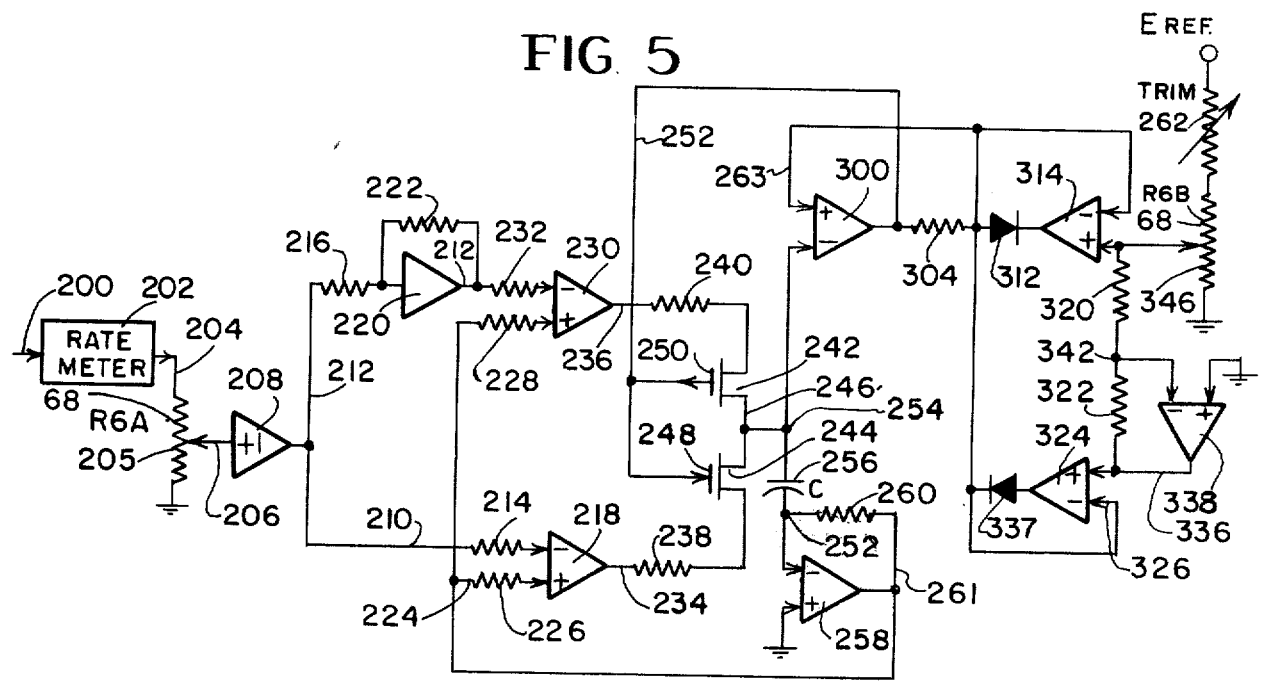
FIG. 5 is a diagram similar to that of FIG. 4 but comprising circuitry including an additional control voltage input.

It is to be emphasized that the clock frequency and the droplet forming frequency are not to be confused. The droplet forming frequency has until now been considered a constant. Since there are other reasons why it may be desirable to change the droplet forming frequency, a third control over the clock frequency, as shown in FIG. 5 is required. A connection 200 in FIG. 3 corresponding to a connection 200 in FIG. 5, provides the third input to the clock oscillator 66.

In the delay means, instead of one or more shift registers an univibrator may be used which puts out a single pulse each time is sensed the duration of which is just sufficient to provide the appropriate delay. The period of the univibrator would be inversely proportional to the distance between droplets. A circuit therefor would be very similar to those shown in FIGS. 4 and 5, except that it goes through only one cycle per particle and resets itself rather than gong through hundred of cycles in this same period and on a continuous basis.

Figure 4:
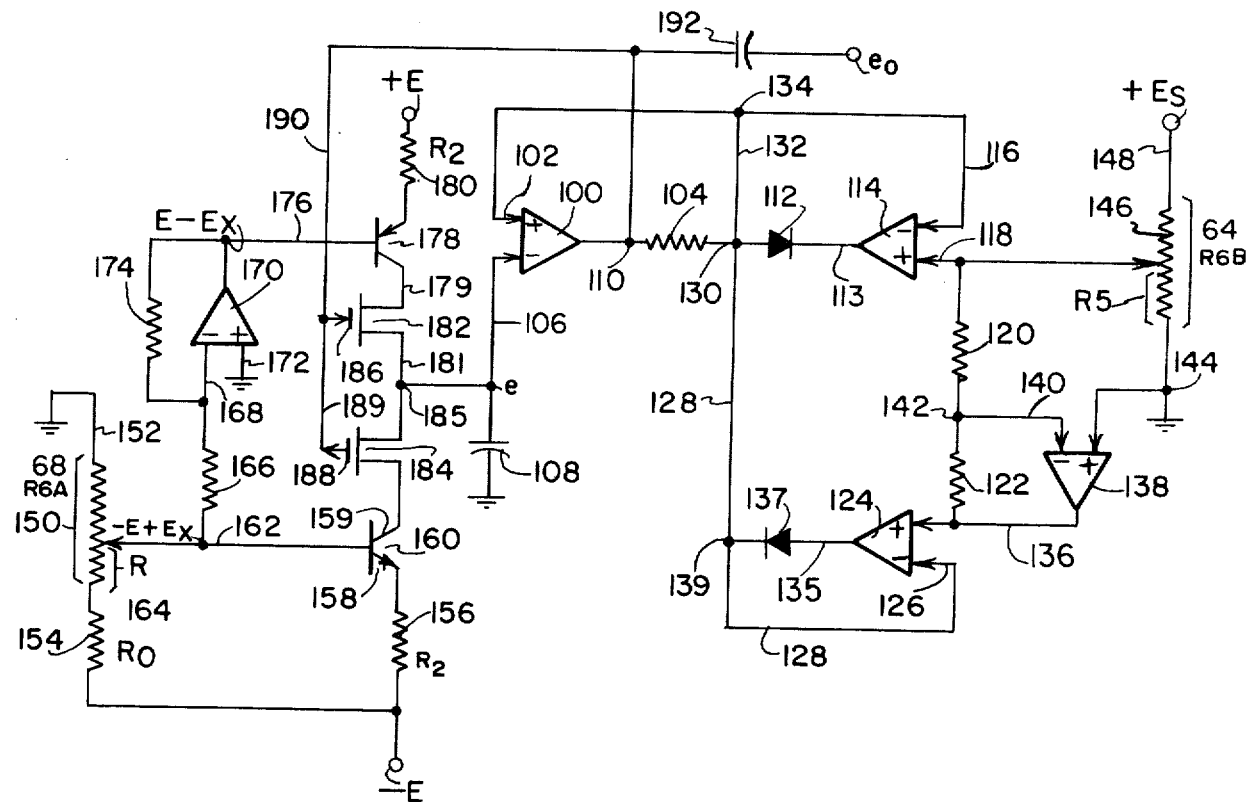
FIG. 4 is a schematic diagram including an oscillator as used in the invention.

FIG. 4 is a circuit based upon a well-known oscillator circuit, which is modified to provide adjustable limits to the peak-to-peak swing and also to linearize the ramp from one peak to another. The circuit is built around an operational amplifier 100 having a positive feedback connection to its non-inverting input 102 through a resistor 104. The inverting input 106 of the amplifier 100 leads over a juncture e to a capacitor 108 which is grounded.

The output 110 of amplifier 100 is coupled via the resistor 104 and a diode 112 to the output 113 of a second operational amplifier 114. The inverting input 116 of amplifier 114 is connected to the non-inverting input 102 of the amplifier 100. The non-inverting input 118 of amplifier 114 leads over resistors 120, 122 to the non-inverting input of an amplifier 124. The inverting input 126 of the amplifier 124 is coupled by line 128 to a node 130 on the line connecting the outputs of amplifiers 100 and 114, the node 130 also being connected over a path 132 to a node 134 on the line connecting the non-inverting output 102 of amplifier 100 with the inverting output 116 of amplifier 114. The output 135 of amplifier 124 is coupled over a diode 137 to the line 128 at a node 139.

The non-inverting input of amplifier 124 is also connected to the output 136 of an amplifier 138. The inverting input 140 of the amplifier 138 is coupled to a node 142 between the resistors 120 and 122, while the non-inverting input of this amplifier 138 is connected to the grounded terminal 144 of a potentiometer 146 also designated as R6B and 64 the function of which will be explained hereinafter. The arm of the potentiometer 146 is coupled to the non-inverting input 118 of amplifier 114 as well as to the resistor 120.

The second or non-ground terminal of potentiometer coil 146 is coupled by a path 148 to a power source + $E_s$. Another potentiometer 150 equivalent to R6A or 68 is coupled over a resistor 154 to a power source $-E$ and over a resistor 156 to the emitter 158 of a transistor 160. The base of transistor 160 is connected by a path 162 to the arm 164 of the potentiometer 150, and also over a resistor 166 to the inverting input 168 of an amplifier 170, the non-inverting input 172 thereof being grounded. The inverting input 168 of amplifier 170 is also coupled via a resistor 174 to the output side of amplfier 170 which in turn is connected by a line 176 to the base of a transistor 178. The emitter of transistor 178 is coupled via a resistor 180 to a power source +E.

A path 179 leads from the collector terminal of the transistor 178 to a MOSFET 182 and over a path 181 to a MOSFET 184 and finally to the collector terminal of transistor 160. The path portion 181 between the MOSFETs 182 and 184 is connected over a node 185 to point $e$.

The gates 186 and 188 of MOSFETs 182 and 184 are connected to one another by line 189 and also over path 190 to the output side of amplifier 100, and are furthermore coupled parallel thereto over a capacitor 192 to a terminal designated $e_o$.

In operation, due to the positive feedback connection of the amplifier 100 to its non-inverting input 102 which is a regenerative connection, the amplifier 100 will be saturated in one direction or the other. When it is at its positive saturation condition, it applies through resistor 104 a voltage to the path 132 which by means of the branch 116 is applied to the inverting input of the amplifier 114. Depending upon the voltage at the non-inverting input 118, its output at 113 will be positive or negative. If it is assumed that the voltage on the capacitor 108 starts at ground potential, the output at 110 of the amplifier 100 will be saturated in the positive direction. However, the voltage at the input 118 of the amplifier 114 is already at some positive voltage. Therefore, the voltage at 116 will be negative, and highly negative at that, with respect to the voltage at 118. This will cause the voltage at 113 to be highly positive and will thus bias off the diode 112. By means to be discussed later, the voltage at e will rise in a positive direction. When it exceeds the voltage at input 102 by a tiny amount, the voltage at 110 will snap to the other or negative saturated condition and this negative voltage will be applied to the input 116 of the operational amplifier 114. Hence, the amplifier 114 will also snap and will apply a negative voltage at 113, causing the diode 112 to conduct strongly. Therefore, the impedance or the apparent impedance at path 132 will be extremely low due to feedback action and the voltage will not change any further, but instead will sit at the voltage level at the input 118 of the amplifier 114.

As mentioned earlier, it is necessary for some means to apply current to the capacitor 108 in order to make the voltage e to rise linearly in the positive direction. This is accomplished by means of the constant current generator comprising the transistor 178 and the resistor 180. The base of this transistor is held at a constant voltage at the path 176. The MOSFET 182 is on at this time and the MOSFET 184 is off. Therefore, current flows from the positive source +E down through the transistor 178 and the MOSFET 182 and charges up the capacitor 108. When the voltage e exceeds the voltage at path 102 and the amplifier 100 snaps from one condition of saturation to another, this voltage is also applied by path 190 to the gates 186 and 188 of the MOSFETs 182 and 184. This causes the MOSFET 182 to be turned off and the MOSFET 184 to be turned on, thus connecting the capacitor 108 to the constant current source comprising transistor 160 and resistor 156 which is an identical constant current source to that of 178 and 180 except having the opposite polarity. Hence, the reverse action takes place and the voltage e ramps linearly downward, that is, in a negative direction. The voltage at 132 is also applied to the amplifier 124 by way of path 126. When the voltage at 126 is more negative than the voltage 136, which is arranged to be the exact opposite of the voltage at 118, the amplifier 124 snaps and causes the diode 137 to conduct heavily, thus, limiting the travel of the voltage at 132 in the negative direction. This voltage also appears at path 102, and hence, the amplifier 100 also snaps, reversing the polarity of the voltage at 112 and starting the cycle all over again.

The rate at which the voltage e changes is proportional to the current which flows in either of the constant current sources and inversely proportional to its capacitance. The voltage which flows in the constant current sources can be explained by observing the action of transistor 160 and its emitter resistor 156. The base 162 of the transistor 160 has its voltage set by the potentiometer R6A or 150 and the fixed resistor $R_o$ or 154, which combination is an attenuator placed across the positive voltage source —E. The voltage at the emitter 158 of the transistor 160 is very nearly equal to that at the base 162, or can be considered so for the time being. In actual practice, it may be necessary to have another identical transistor or a diode to compensate for the base-emitter junction voltage. The present circuit of FIG. 4 has omitted such details in order to facilitate explanation. Assuming that the emitter 158 is at the same voltage as the base 162, the current in the emitter resistor 156 will be equal to the voltage at the arm 164 of the potentiometer R6A or 150 from the voltage —E divided by the resistance 156 which, must flow to the collector 159 through the MOSFET 184 and into the capacitor 108.

The circuit in FIG. 5 has the same basic idea as that in FIG. 4 but comprises modified means for providing constant current to the capacitor 108 and also includes a third control input for use in compensating for variations in droplet-forming frequency as indicated earlier.

The circuit shows on the left side an input line 200 for receiving pulses from the generator 23 as shown in FIG. 3. The line 200 is the input to a ratemeter 202 whose function will subsequently be explained. The output 204 of the ratemeter is coupled via a grounded potentiometer 205 or R6A and its arm 206 to an amplifier 208. The output of amplifier 208 is coupled in parallel lines 210 and 212 and resistors 214 and 216 respectively to amplifiers 218 and 220. The amplifier 220 is provided with a resistor 222 in its feedback path. The amplifier 218 has a second input 224 with a resistor 226 which is coupled over a resistor 228 to the non-inverting input of an amplifier 230. The inverting input of the amplifier 230 is coupled over a resistor 232 to the output of the amplifier 220. The outputs 234 and 236 of amplifiers 218 and 230 respectively are coupled via resistors 238 and 240 to MOSFET switches 242 and 244 which are connected to one another by a line 246. The gates 248 and 250 are connected in parallel via a path 252 to the output of an amplifier 300, which is the equivalent of amplifier 100 in FIG. 4.

The line 246 connecting the MOSFET switches 242 and 244 is connected to a node 254 which is coupled to one terminal of a capacitor 256 being the equivalent of the capacitor 108 in FIG. 4. Another lead from the node 254 extends to the second input of the amplifier 300.

The other terminal of the capacitor 256 is connected to an amplifier 258 whose second input is grounded. A resistor 260 is provided in the feedback loop of the amplifier 258. The output of the amplifier 258 is connected in parallel to the second inputs of amplifiers 218 and 230.

The amplifiers 300, 314, 324 and 338 are the equivalents of the amplifiers 100, 114, 124 and 138 of FIG. 4. Analogously all the connections between these amplifiers in FIG. 5 are respectively the same as the corresponding connections in FIG. 4. The reference numerals for these elements in FIG. 5 have been chosen to be in the 300 group while the corresponding elements in FIG. 4 are in the 100 group, but the tens and units are the same in both circuits. There is, however, an exception as follows. The non-grounded terminal of the potentiometer 346 or R6B is coupled to a variable trim resistor 262 which in turn is connected to a reference potential $E_{REF}$.

Considering the operation of the circuit in FIG. 5, it is to be noted that it provides for the ground reference input terminal 200 which permits the frequency to be a function of the frequency of the droplet-forming transducer or generator as well as the rotation of the potentiometer R6A. The pulses from the droplet-forming generator are applied to terminal 200 and to the ratemeter 202 which translates the frequency of the droplet-forming oscillator into a proportional d.c. voltage. This d.c. voltage appears at path 204 and, hence, at the potentiometer R6A or 205 which also appears in FIG. 4 as 150. The voltage at the arm 206 of the potentiometer 205 is thus proportional to the product of the droplet-forming frequency and the rotation of the variable graticule. The amplifier 208 is a unity gain amplifier which serves to remove resistive loading from the arm 206 of the potentiometer R6A or 205 so that it is not made non-linear. This voltage is applied to the path 210 directly and to the path 212 via the inverting amplifier including the operational amplifier 220 and the resistors 216 and 222. The switches which determine whether the current to the capacitor 256 is positive or negative again comprise the MOSFETS 242 and 244. The capacitor 256, instead of being grounded directly as in FIG. 4, is connected instead to the node 257 of the operational amplifier 258. The feedback provided around this amplifier by the resistor 260 causes the impedance from the node 257 to ground to be practically zero. However, the current which flows in the capacitor 256 must flow in the resistor 260 and, hence, produces at the output 261 of the operational amplifier 258 a voltage which is proportional to the current flowing in the capacitor. Depending upon whether MOSFET 242 or 244 is conducting, the current will come from either the operational amplifier 230 or 218. When the MOSFET 242 is conducting, the current will come from the operational amplifier 230 and will be such that the voltage at the output 261 of the operational amplifier 258 will be negative. Feedback will cause this voltage to be exactly equal to the voltage at the path 212 and, thus will insure that the current flowing the the capacitor 256 is not only constant, but proportional to the voltage at 212 and, hence, to the voltage at 206. When the voltage at the top connection of the capacitor at 254 crosses the voltage at the input 238 of the operational amplifier 300, the operational amplifier 300 will snap, turning off MOSFET 242 and turning on MOSFET 244. The current to the capacitor 256 will now come from operational amplifier 218, the voltage at the output 261 of the operational amplifier 258 will fly positive until the voltage at the input 224 of the operational amplifier 218 is equal to the voltage at the path 210 and, thus, will be exactly equal and opposite to the current in the capacitor 256 during the previous half cycle. When the voltage at 254 again crosses the voltage 263, the circuit will snap and the cycle will be repeated ad infinitum.

These oscillator circuits will be appreciated for novel features residing in the method of limiting the peak-to-peak swing and in furnishing constant current to the capacitor 108 or 256.

FIG. 6 is, as indicated earlier, a modification of FIG. 3 to show a simple variable delay univibrator 400 primarily in place of the clock oscillator 66 and shift registers 78, 80, 82. The same two potentiometers R6A and R6B or 68 and 64 are used to adjust the slope and trigger level or amplitude of the saw put out by the univibrator as used in the free running oscillator of FIGS. 4 and 5. The univibrator 400 essentially is the same except that it ramps in only one direction, resets and waits at the end of each ramp for the following particle.

In further detail, the linear potentiometer 64 (R6B) is connected to height adjustment member 58 just as in FIG. 3. The linear potentiometer 68 (R6A) is connected analogously to the graticule 46.

On the output side of the univibrator 400 there is provided an edge detector 402, its output being connected to a single shot univibrator 404 which in turn is connected to the charging plates 33–35, analogous to the arrangement in FIG. 3.

FIG. 7 is to explain how the univibrator 400 works. The structure includes on the left side an input coming from a rate meter, just as in FIG. 5, but here labeled a frequency to DC converter, connected over a buffer amplifier, which is optional, and continuing over a line 204 to the gounded potentiometer 68 or R6A. The line 204 has a voltage $e_t$. The slider 206 of the potentiometer 68 has a voltage $e_t$ $\theta$; $\theta$ being the rotation angle of the slider which is connected to the input of the amplifier 208, just as in FIG. 5.

The output of the amplifier 208 is connected via the resistor 216 to an amplifier 404 having a first feedback loop including the capacitor 108, and a second feedback loop including an FET 406. The right junction point of the first feedback loop has the voltage $e_2$ and is connected to a first input of a comparator 408. The second input of the comparator 408 comes from the slider of the potentiometer 64 or R6B. The input of the potentiometer 64 or R6B is joined to a voltage $E_s$. Thus, a voltage $E_s\phi$ is applied to the second input of the comparator 408; $\phi$ being the rotation angle of the slider. The output side of the potentiometer 64 is grounded.

The output of the comparator 408 is connected to the reset input of an RS flip flop 410; the set input of the flip flop coming from the trigger line. The output Q of the flip flop is connected to the base of the FET 406. Also connected to the base of the FET 406 is a line that carries the output pulse of the univibrator.

In operation, when a trigger pulse occurs as a particle pulse the RS flip flop is set, biasing the FET beyond pinch-off and permitting charging current $e_t\theta/R_2$ to flow into the capacitor 108, charging the capacitor 108 to voltage $e_t\, t/R_2 C$.

When $e_2$ exceeds $E_s\phi$, the comparator 408 changes its output state, applying a reset pulse to the RS flip flop, in which state the capacitor 108 is shorted out. Duration of the output pulse is proportional to voltage $E_s\phi$ and hence to the angular position of the potentiometer R6B or 64, and inversely proportional to the product of the repition rate of the droplet forming generator times angular position of the graticule.

Figure 8:
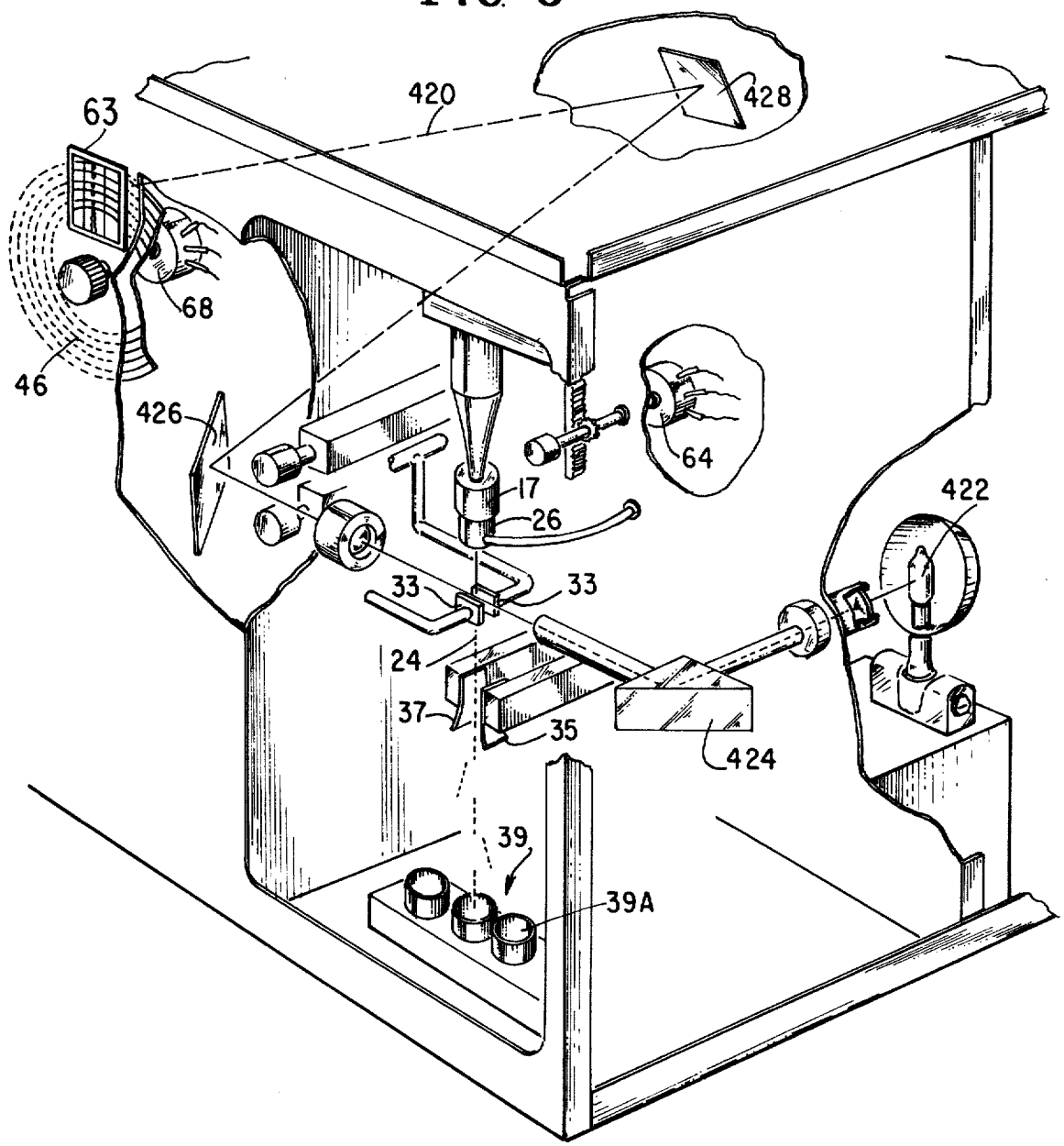
FIG. 8 is a partial perspective view of the particle separator.

FIG. 8 is a partial view of the particle separator unit. As is readily noticeable, there are the two potentiometers 68 and 64. Potentiometer 68 is driven by the same shaft as the spiral graticule 46. The other potentiometer 64 is driven by the same shaft that raises and lowers the jet-forming nozzle assembly 17. In actuality, the height adjustment may be accomplished by a worm gear in order to get the fine adjustment; however, the drawing shows a rack and pinion, since it can be shown much more simply and clearly. Also, a light beam 420 is shown starting from a lamp 422, being reflected by a prism 424 and two mirrors 426, 428 and ending at the graticule 46.

Finally, mention may be made of the charging plates 33 and deflecting plates 35, 37. The remainder of the elements are the same as previously described and, as it is believed, do not have to be particularly mentioned here.

Finally, a brief explanation of the way in which the operator may handle the adjusting delay device in the particle separator would be as follows.

The operator adjusts the jet sideways to bring the image on the ground glass screen, which also fixes the magnification. Further he adjusts it back and/or forth to line up the jet with a permanent vertical line on the screen, and finally he adjusts the nozzle up and down until the break-off point lines up with the base circle on the dial. Then the scale is rotated until the image of a droplet is on each of the intersections of the spirals with the vertical line. By so doing, the clock oscillator is automatically set at that frequency which causes the shift register(s) to provide the correct delay.

It is believed that the foregoing adequately will enable those skilled in the art to appreciate and practice this invention and, if necessary, make modifications which would fall within the scope of the invention as defined by the accompanying claims.

As an example, an alternative arrangement to that shown in FIG. 2 would be a roll such as of photographic film, which would be adjusted by rolling it from one reel to another. Proper spacing between the graticule lines would be found or calculated, and then potentiometer R6A could be coupled mechanically to either of the reels. This arrangement would occupy less space if space were a problem.

What is claimed and desired to be secured by Letters Patent of the United States is:

1. A device for adjusting an electrical delay to a time interval between two occurrences of a moving particle in an apparatus for classifying particles suspended in a fluid, in which said apparatus comprises:
  A. nozzle means including a nozzle connected to a fluid reservoir for generating a fluid jet,
  B. means connected to the nozzle means for pulsating the fluid jet so as to separate same into droplets at a break-off point,
  C. sensing means located at the outlet of the nozzle means for producing an electric quantity in response to a selected parameter of a passing particle,
  D. means disposed adjacent the fluid downstream of the sensing means for charging each droplet with a potential related to the electric quantity produced by the sensing means,
  E. electrical delay means, the input thereof being coupled to the sensing means and the output thereof being coupled to the charging means,
  F. first and second means associated with the electrical delay means for adjusting the delay of said electrical delay means,
  G. means situated downstream of the charging means for deflecting each droplet by an amount related to said parameter of the particle,
  H. collecting means supported downstream of the deflecting means for collecting the droplets in relation to the amounts of deflection,
  I. microscope means arranged in front of the nozzle means and means for illuminating same in synchronization with said pulsating means,
  J. movable scale means associated with the microscope means and including a graticule having a reference line and at least one nonparallel comparison line,
  K. position adjusting means connected to the nozzle means for raising or lowering the nozzle until the image of the breakoff point of the jet is on said reference line,
  L. graticule adjusting means associated with the graticule for aligning said at least one comparison line with the image of at least one of said droplets, and
  M. means for coupling said first and second delay adjusting means to said position and graticule adjusting means, respectively.

wherein, upon completion of said adjustments, the image of the train of droplets is rendered visible, stationary and measurable, and the electrical delay is substantially equal to the time interval between the passage of a particle through the sensing means and the arrival thereof at the break-off point.

2. The device as set forth in claim 1 in which the microscope means comprise a projection microscope and the illuminating means include a stroboscopic light source.

3. The device as set forth in claim 1 in which the movable scale means is coupled to a potentiometer of a RC oscillator for controlling the frequency thereof.

4. The device as set forth in claim 1 including a third adjustment means connected to the nozzle means for placing the jet emerging from the nozzle in the optimum distance from the microscope objective lens.

5. The device as set forth in claim 4 in which the microscope includes prism means for facilitating obtaining a clear image.

6. The device as set forth in claim 1 including a fourth adjustment means for centering the image in the screen.

7. The device as set forth in claim 1 in which said electrical delay means comprises at least one shift register.

8. The device as set forth in claim 1 comprising univibrator means including means for setting the delay time thereof inversely proportional to the distance between droplets.

9. The device as set forth in claim 1 comprising univibrator means including means for setting the delay time thereof directly proportional to the distance between said sensing means and said breakoff point.

10. The device as set forth in claim 1 in which the droplet forming generator includes means for controlling the frequency which controls said electric delay means.

11. The device as set forth in claim 1 including an oscillator circuit comprising a capacitor and means for limiting the peak-to-peak swing and linearizing the ramp from one peak to the other.

12. The device as set forth in claim 11 including first means for providing constant current to the capacitor of the oscillator circuit.

13. The device as set forth in claim 11 including second means for providing constant current to the capacitor of the oscillator circuit.

* * * * *